US012599591B2

(12) United States Patent
Marjomäki et al.

(10) Patent No.: US 12,599,591 B2
(45) Date of Patent: Apr. 14, 2026

(54) VEMURAFENIB AND SALTS THEREOF FOR USE IN THE TREATMENT OF ENTEROVIRAL INFECTIONS

(71) Applicant: Jyväskylän yliopisto, Jyväskylän yliopisto (FI)

(72) Inventors: Varpu Marjomäki, Jyväskylä (FI); Mira Laajala, Jyväskylä (FI); Mari Martikainen, Jyväskylä (FI)

(73) Assignee: Jyväskylän yliopisto, Jyväskylän yliopisto (FI)

(*) Notice: Subject to any disclaimer, the term of this patent is extended or adjusted under 35 U.S.C. 154(b) by 622 days.

(21) Appl. No.: 17/281,650

(22) PCT Filed: Oct. 3, 2019

(86) PCT No.: PCT/FI2019/050712
§ 371 (c)(1),
(2) Date: Mar. 31, 2021

(87) PCT Pub. No.: WO2020/070390
PCT Pub. Date: Apr. 9, 2020

(65) Prior Publication Data

US 2021/0244716 A1 Aug. 12, 2021

(30) Foreign Application Priority Data

Oct. 3, 2018 (FI) .................................... 20185830

(51) Int. Cl.

| | |
|---|---|
| ***A61K 31/437*** | (2006.01) |
| ***A61K 9/00*** | (2006.01) |
| ***A61K 9/20*** | (2006.01) |
| ***A61P 31/16*** | (2006.01) |

(52) U.S. Cl.
CPC .......... *A61K 31/437* (2013.01); *A61K 9/0053* (2013.01); *A61K 9/2009* (2013.01); *A61K 9/2013* (2013.01); *A61K 9/2054* (2013.01); *A61P 31/16* (2018.01)

(58) Field of Classification Search
CPC .. A61K 31/437; A61K 9/0053; A61K 9/2009; A61K 9/2013; A61K 9/2054; A61P 31/16; Y02A 50/30
See application file for complete search history.

(56) References Cited

U.S. PATENT DOCUMENTS

| | | | | |
|---|---|---|---|---|
| 9,566,281 | B2 * | 2/2017 | Pleschka | A61P 31/16 |
| 2016/0016950 | A1 * | 1/2016 | Albrecht | A61P 43/00 546/113 |
| 2016/0068530 | A1 | 3/2016 | Lehmann et al. | |
| 2017/0320872 | A1 | 11/2017 | Prashant et al. | |

FOREIGN PATENT DOCUMENTS

| | | | | |
|---|---|---|---|---|
| WO | WO9418960 | A1 | 9/1994 | |
| WO | WO2007002433 | A1 | 1/2007 | |
| WO | WO2011160191 | A1 | 12/2011 | |
| WO | WO2014056894 | A1 | 4/2014 | |
| WO | WO-2016073421 | A1 * | 5/2016 | A61K 31/18 |
| WO | WO2016165678 | A1 | 10/2016 | |
| WO | WO2017147526 | A1 | 8/2017 | |
| WO | WO2018002415 | A1 | 1/2018 | |

OTHER PUBLICATIONS

Stuart, S. A., Houel, S., Lee, T., Wang, N., Old, W. M., & Ahn, N. G. A Phosphoproteomic Comparison of B-RAFV600E and MKK1/2 Inhibitors in Melanoma Cells. Molecular & Cellular Proteomics: MCP, 14(6), 1599-1615. https://doi.org/10.1074/mcp.M114.047233 (Year: 2015).*
Van der Schaar et al. A Novel, Broad-Spectrum Inhibitor of Enterovirus Replication That Targets Host Cell Factor Phosphatidylinositol 4-Kinase IIIβ. Antimicrobial Agents and Chemotherapy, 57(10), 4971-4981. https://doi.org/10.1128/aac.01175-13 (Year: 2013).*
Committee for Medicinal Products for Human Use. Zelboraf Assessment Report (Year: 2012).*
Garmaroudi, F. S., Marchant, D., Hendry, R., Luo, H., Yang, D., Ye, X., Shi, J., & McManus, B. M. Coxsackievirus B3 replication and pathogenesis. Future Microbiology, 10(4), 629-653. https://doi.org/10.2217/fmb.15.5 (Year: 2015).*
Pleschka, S. RNA viruses and the mitogenic Raf/MEK/ERK signal transduction cascade. Biological Chemistry, 389(10). https://doi.org/10.1515/bc.2008.145 (Year: 2008).*
Alidjinou et al: Persistent infection of human pancreatic cells with Coxsackievirus B4 is cured by fluoxetine. Antiviral Research, Apr. 2015, vol. 116, pp. 51-54.
Bollag et al: Clinical efficacy of a RAF inhibitor needs broad target blockade in BRAF-mutant melanoma. Nature, 2010, vol. 467, No. 7315, pp. 596-599.
Chapman et al: Improved Survival with Vemurafenib in Melanoma with BRAF V600E Mutation. N Engl J Med., Jun. 30, 2011, vol. 364, No. 26, pp. 2507-2516.
Feng et al: Enterovirus 2Apro Targets MDA5 and MAVS in Infected Cells. Journal of Virology, Mar. 2014, vol. 88, No. 6, pp. 3369-3378.
Krzyzaniak et al: Host Cell Entry of Respiratory Syncytial Virus Involves Macropinocytosis Followed by Proteolytic Activation of the F Protein. PLOS Pathogens, Apr. 2013, vol. 9, Issue 4.
Laitinen et al: New Coxsackievirus 2Apro and 3Cpro protease antibodies for virus detection and discovery of pathogenic mechanisms. Journal of Virological Methods, 2018, vol. 255, pp. 29-37.
Marjomäki et al: Internalization of Echovirus 1 in Caveolae. Journal of Virology, Feb. 2002, vol. 76, No. 4, pp. 1856-1865.

(Continued)

*Primary Examiner* — Scarlett Y Goon
*Assistant Examiner* — Hoi Yan Lee
(74) *Attorney, Agent, or Firm* — Laine IP Oy

(57) ABSTRACT

The present invention provides N-(3-(5-(4-chlorophenyl)-1H-pyrrolo[2,3-b]pyridine-3-carbonyl)-2,4-difluorophenyl) propane-1-sulfonamide known as vemurafenib, and pharmaceutical salts thereof for use in the treatment of enteroviral diseases.

14 Claims, 10 Drawing Sheets

Specification includes a Sequence Listing.

(56) References Cited

OTHER PUBLICATIONS

Martikainen et al: Hydrophobic pocket targeting probes for enteroviruses. Nanoscale, 2015, vol. 7, No. 41, pp. 17457-17467.
McKimm-Breschkin et al: Meeting report: 4th ISIRV antiviral group conference: Novel antiviral therapies for influenza and other respiratory viruses. Antiviral Research, Feb. 9, 2016, vol. 129, No. 21-38, p. 28.
Myllynen et al: A Novel Open and Infectious Form of Echovirus 1. Journal of Virology, Aug. 2016, vol. 90, No. 15, pp. 6759-6770.
Oh et al: Paradoxical activation of MEK/ERK signaling induced by B-Raf inhibition enhances DR5 expression and DR5 activation-induced apoptosis in Ras-mutant cancer cells. Scientific Reports, May 25, 2016.
Pelkmans et al: Genome-wide analysis of human kinases in clathrin- and caveolae/raftmediated endocytosis. Nature, Jul. 2005, vol. 436.
Spuul et al: Assembly of Alphavirus Replication Complexes from RNA and Protein Components in a Novel trans-Replication System in Mammalian Cells. Journal of Virology, Feb. 2011, vol. 85, No. 10, pp. 4739-4751.

* cited by examiner

| TargetID | -/- | -/Vemu | EV1/- | EV1/Vemu |
|---|---|---|---|---|
| RN5S9 | 0 | 0,01 | 5,35 | 0,80 |
| LOC100008589 | 0 | 0,12 | 4,98 | 0,12 |
| SNORD3D | 0 | 0,20 | 4,10 | 0,18 |
| LOC100132564 | 0 | 0,36 | 3,48 | 0,14 |
| LOC100134364 | 0 | -0,30 | 3,14 | -0,21 |
| LOC100008589 | 0 | -0,16 | 2,97 | -0,15 |
| LOC100133394 | 0 | -0,10 | 2,37 | -0,13 |
| RMRP | 0 | 0,02 | 2,30 | 0,10 |
| MIR1978 | 0 | -0,09 | 2,19 | -0,08 |
| RNU1A3 | 0 | -0,02 | 2,12 | 0,89 |
| LOC728844 | 0 | 0,10 | 2,06 | 2,94 |
| | | | | |
| HS.25318 | 0 | 0,36 | -2,00 | -0,86 |
| HS.100261 | 0 | -0,20 | -2,01 | -1,40 |
| CDH2 | 0 | -0,13 | -2,01 | -1,05 |
| NCKAP1 | 0 | -0,05 | -2,01 | -0,74 |
| SLC27A2 | 0 | -0,24 | -2,03 | -0,70 |
| KRT19 | 0 | -0,03 | -2,04 | -0,46 |
| CBARA1 | 0 | -0,15 | -2,06 | -0,38 |
| EEF1D | 0 | 0,11 | -2,07 | -0,30 |
| ACTA2 | 0 | -0,09 | -2,07 | -0,51 |
| MMP7 | 0 | -0,26 | -2,08 | -0,57 |
| C11ORF68 | 0 | -0,42 | -2,09 | -0,67 |
| CROP | 0 | 0,24 | -2,11 | -0,09 |
| ANKFY1 | 0 | 0,07 | -2,13 | -0,71 |
| SYT13 | 0 | -0,11 | -2,23 | -0,42 |
| LOC441484 | 0 | -0,01 | -2,23 | -0,12 |
| RAB31 | 0 | 0,31 | -2,28 | -0,28 |
| EXOSC2 | 0 | -0,30 | -2,33 | -0,44 |
| CEACAM6 | 0 | 0,24 | -2,35 | -0,74 |
| DAZAP1 | 0 | -0,09 | -2,44 | -0,52 |
| SARS | 0 | 0,79 | -2,63 | -0,14 |
| KIFAP3 | 0 | -0,08 | -2,70 | -0,89 |
| SDHAF2 | 0 | -0,22 | -2,93 | -0,18 |
| COPS3 | 0 | -0,01 | -3,85 | -0,50 |

Most up-regulated mRNAs

Most down-regulated mRNAs

Figure 7.

| | | D7 | D9 | D14 | D21 |
|---|---|---|---|---|---|
| Intracellular viral RNA | | + | + | – | – |

SEQUENCE LISTING

```
<160> NUMBER OF SEQ ID NOS: 2

<210> SEQ ID NO 1
<211> LENGTH: 48
<212> TYPE: DNA
<213> ORGANISM: Artificial
<220> FEATURE:
<223> OTHER INFORMATION: Polymerase primer

<400> SEQUENCE: 1

aucacgucau cucacucuac aucacuggcg cccgggtaau cgggcgcc                48


<210> SEQ ID NO 2
<211> LENGTH: 37
<212> TYPE: DNA
<213> ORGANISM: Artificial
<220> FEATURE:
<223> OTHER INFORMATION: Polymerase primer

<400> SEQUENCE: 2

aucacgacau cacuggcgcc cgggtaaucg ggcgcca                            37
```

VEMURAFENIB AND SALTS THEREOF FOR USE IN THE TREATMENT OF ENTEROVIRAL INFECTIONS

FIELD OF THE INVENTION

The present invention is related to the field of medicine and particularly to vemurafenib, i.e. N-(3-(5-(4-chlorophenyl)-1H-pyrrolo[2,3-b]pyridine-3-carbonyl)-2,4-difluorophenyl) propane-1-sulfonamide, and pharmaceutical salts thereof for use in the treatment of enteroviral infections.

BACKGROUND OF THE INVENTION

The compound N-(3-(5-(4-chlorophenyl)-1H-pyrrolo[2,3-b]pyridine-3-carbonyl)-2,4-difluorophenyl)propane-1-sulfonamide (vemurafenib) is known as a BRAF enzyme inhibitor effective for the treatment of cancers such as metastatic melanoma, thyroid cancers and colorectal cancers. BRAF is a serine/threonine kinase of the RAF family that acts in the RAF/MEK/ERK signaling pathway, which normally regulates cell growth, survival and differentiation. Mutations of the kinase lead to overactive signaling and hence excessive proliferation and survival of cancer cells. Vemurafenib inhibits v600eBRAF by directly binding to the kinase and blocking the activated pathway and downstream signaling (Bollag et al., 2010). The compound has the chemical formula (I) presented below.

(I)

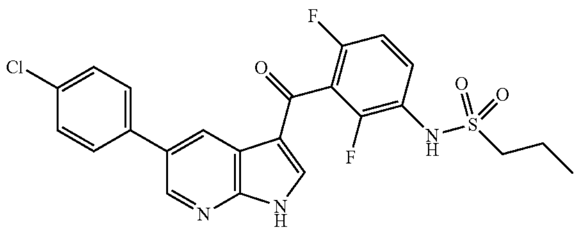

Vemurafenib (also known as PLX4032 or RG7204) was approved by the FDA for the treatment of metastatic or unresectable melanoma in 2011, based on clinical BRIM-3 studies (Chapman et al., 2011).

Enterovirus infections are among the most common infections affecting humans worldwide. The symptoms vary from common cold to more serious symptoms such as hand-foot-and-mouth disease, meningitis, myocarditis, pancreatitis and poliomyelitis. Enterovirus genus belongs to the family of non-enveloped Picornaviridae and is comprised of twelve species, Enterovirus A-H, and J and Rhinovirus A-C. Enteroviruses cause severe outbreaks, but are also recently associated with chronic diseases such as type I diabetes, asthma and allergies.

WO 9418960 is disclosing the use of 2-chloro-1-[[4-[(2, 6dichlorophenoxy) methyl]phenyl]methoxy]-4-methoxybenzene for the preparation of a medicament for the selective therapeutic and prophylactic treatment of enteroviral infections in humans.

WO 2011160191 discloses the treatment, alleviation, prevention or reduction in the incidence of symptoms, diseases or conditions resulting from or associated with enteroviruses, more particularly the enteroviral infections they cause, via the administration of 3-ethoxy-6-{2-[1-(6-methylpyridazin-3-yl)-piperidin-4-yl]-ethoxy}-benzo[d]isoxazole.

WO 2014056894 discloses vemurafenib (PLX4032) as a dual Raf-MEK-inhibitor and for use in the treatment or prophylaxis of influenza virus, subtypes A and B.

McKimm-Breschkin et al., focus on the development of inhibitors of several virus targets and key host cell factors involved in virus replication and in mediating inflammatory response in patient. The authors also note that the Raf inhibitor vemurafenib (PLX4032) has shown greater efficacy than oseltamivir against influenza A(H1N1)pdm09 infection.

WO 2017147526 discloses substituted 3-(2-amino-thiazol-5-yl)-benzenesulfonamide compounds as PI4-kinase inhibitors and for use in the treatment of enteroviral infections. WO 2017147526 does not disclose vemurafenib.

The present invention is thus the first to provide results showing that vemurafenib is potentially acting against a wide range of disease-causing enteroviruses.

BRIEF DESCRIPTION OF THE FIGURES

FIG. 7. Vemurafenib shows efficacy in mRNA level during EV1 infection. A transcriptomics study was performed in A549 cells+/−treatment with vemurafenib in the presence of absence of EV1 infection. RNA was extracted from EV1- or mock-infected A549 cells 6 h pi. Gene expression profiling was done using Illumina Human HT-12 v4 Expression BeadChip Kit according to manufacturer's recommendation. Genes differentially expressed between samples and controls were determined using the Limma package. Benjamini-Hocberg multiple correction testing method was used to filter out differentially expressed genes based on a q-value threshold ($q<0.05$). Filtered data were sorted by logarithmic fold change (log 2Fc). The data revealed the efficacy of the drug on mRNA level. Several different mRNAs were up- or downregulated due to EV1 but the drug attenuated almost all the effects of the virus.

DETAILED DESCRIPTION OF THE PRESENT INVENTION

Vemurafenib's chemical name is N-(3-(5-(4-chlorophenyl)-1H-pyrrolo[2,3-b]pyridine-3-carbonyl)-2,4-difluorophenyl)propane-1-sulfonamide or propane-1-sulfonic acid {3-[5-(4-chloro-phenyl)-1H-pyrrolo[2,3-b]pyridine-3-carbonyl]-2,4-difluoro-phenyl}-amide. Suitable salts of vemurafenib are disclosed, e.g., in US20170320872 and US20160068530. Synthesis of vemurafenib was first described in WO 2007002433. A novel method for synthesis is disclosed in WO 2018002415. Further amorphous forms of vemurafenib are disclosed in WO 2016165678. Vemurafenib is currently on market as a prescription medicine comprising a co-precipitate of amorphous vemurafenib and hypromellose acetate succinate with colloidal anhydrous silica, croscarmellose sodium, hydroxypropylcellulose, and magnesium stearate as excipients.

Figure 1:
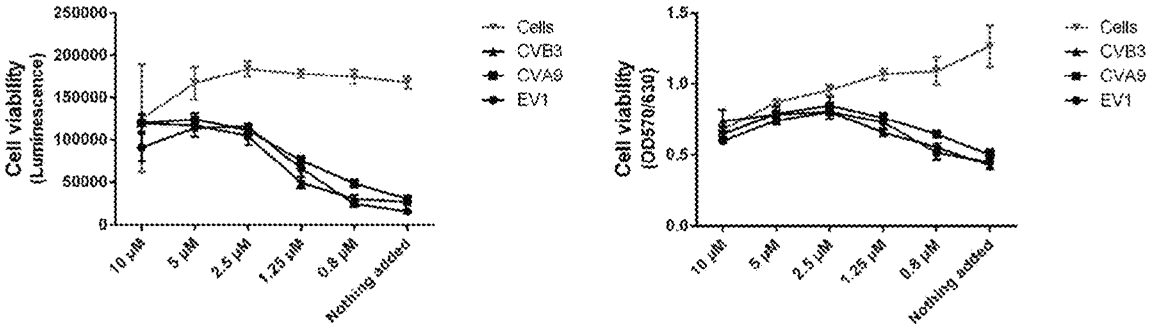
FIG. 1. Vemurafenib prevents the infection of EV1, CVA9 and CVB3 in dose dependent manner. A549 cells were treated for 1 h with different concentrations of vemurafenib before Echovirus 1 (EV1), Coxsackie virus B3 (CVB3) or Coxsackie virus A9 (CVA9) infection, and vemurafenib was present after addition of viruses. Further, non-infected control cells were included. After 18 h post infection, the cell viability was determined by cell viability Glo-titer assay according to the instructions by the manufacturer (CTG assay, which measures cellular ATP levels, Promega; left figure) or crystal violet staining as described before (right figure; Martikainen et al., 2015). Values are means±SD.
Figure 2:
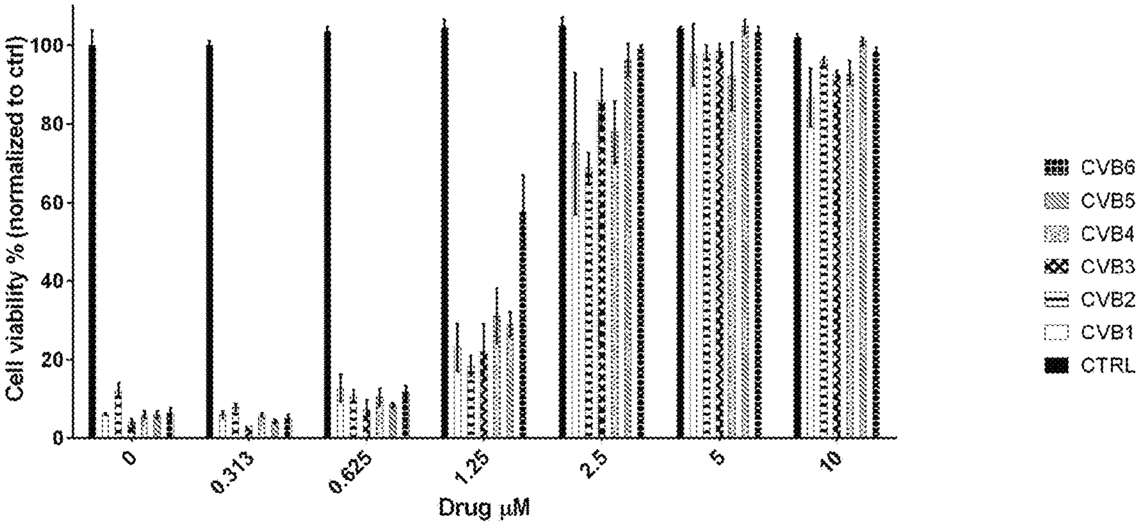
FIG. 2. Vemurafenib prevents the infection of different CVB serotypes in dose dependent manner. Different concentrations of vemurafenib were tested against different Coxsackie virus B (CVB) serotypes (1-6) by treating A549 cells with the drug for 1 h and then infecting the cells with the viruses. Cell viability was determined after 18 h of infection using crystal violet staining. The results were normalized to control sample with no virus infection and 0 μM concentration of vemurafenib (CTRL). The values are means±SD.
Figure 4:
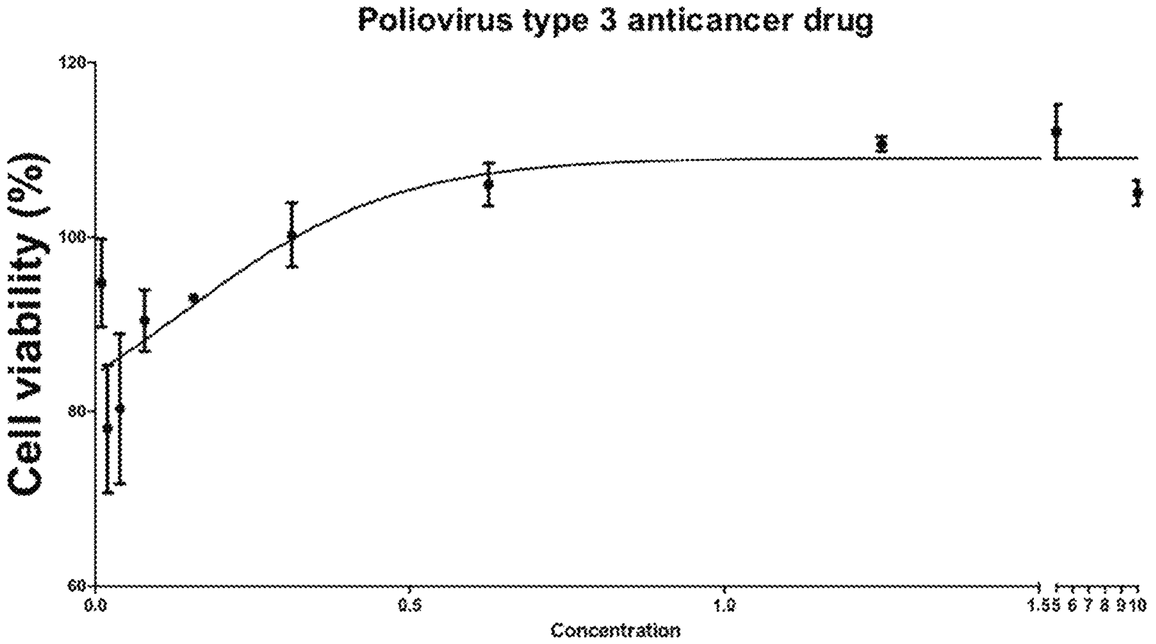
FIG. 4. Vemurafenib prevents the infection of Poliovirus 3 in dose dependent manner. Different concentrations of vemurafenib were tested against polio-3 by treating A549 cells with the drug for 1 h and then infecting the cells with the virus. Cell viability was determined using Cell Titer Glo kit (Promega) after 2 days of infection. The results are means±SD.
Figure 5:
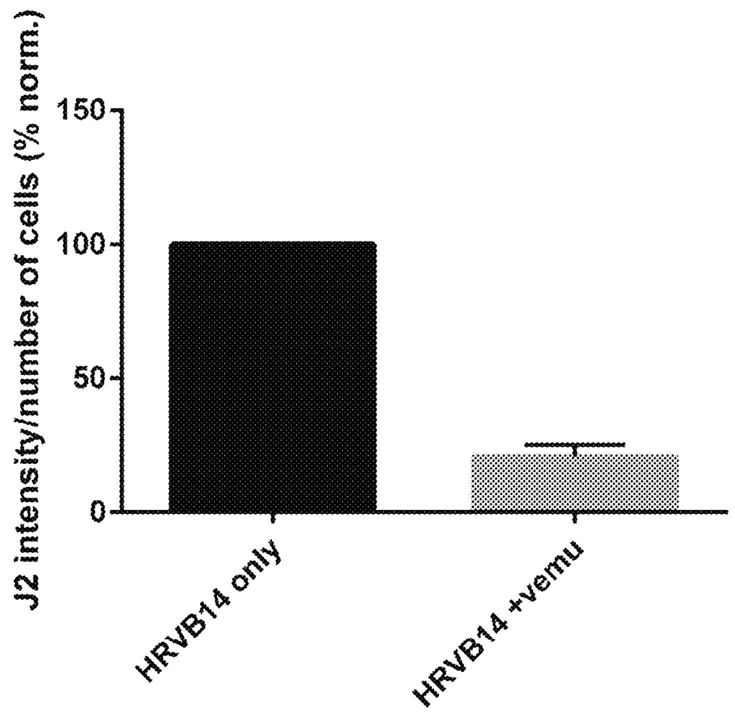
FIG. 5. The drug decreases the replication of human rhinovirus B14 (HRVB14) indicated by labeling of dsRNA. Hela cells were infected with HRVB14 with or without 5 μM vemurafenib and infection was allowed to proceed for 6 h at +34° C. After fixation with 4% PFA, the cells were immunolabeled with dsRNA antibody (J2) in order to determine the status of replication. The intensity of J2 signal was calculated using BioimageXD software. The J2 intesity was normalized to the total number of cells determined by DAPI staining. Finally the results were normalized to HRVB14 infection without the drug which was set to 100%. Values are means from two separate experiments±SD.
Figure 6:
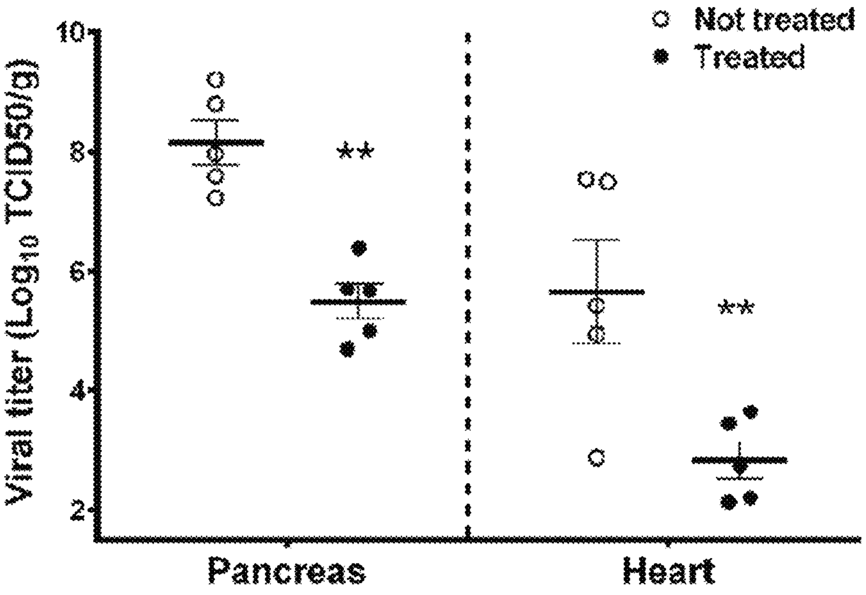
FIG. 6. Vemurafenib decreases the levels of infectious CVB4 viral particles in the heart and pancreas tissue of mice. Hsd:ICR(CD-1) female mice at the age of 3 weeks were inoculated intraperitoneally with Vemurafenib dissolved in DMSO and diluted in PBS (10 mg/kg) or with DMSO diluted in PBS once a day (starting on day 1) for 5 days. The animals were inoculated intraperitoneally with CV-B4 E2 on day 2. The animals were sacrificed on day 6, blood was collected and portions of each organ (pancreas and heart) were frozen for determination of viral titer. Frozen organs were weighed, crushed and homogenized in PBS and then centrifuged at 2000 g for 10 min 4° C. The supernatants were harvested to measure the titer of infectious particles (on HEp-2 cells) and titers were normalized to tissue weight. The results are expressed as log TCID50/g. The limit of detection of the test was 0.75 log TCID50/g.
Figure 8:
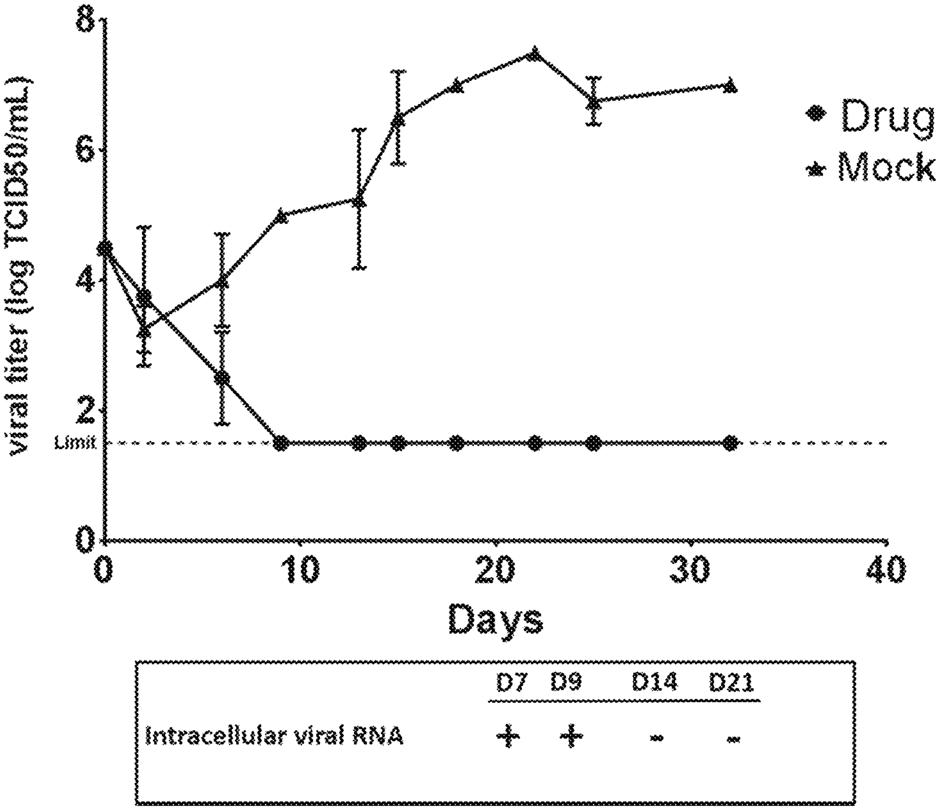
FIG. 8. Vemurafenib eradicates persistent CVB4 infection. Level of infectious viral particles in persistently infected Panc-1 cells was determined by quantifying the viral titers in the supernatant of treated (circles) and untreated cells (triangles). The values are means±SD from two experiments. In addition, the presence of viral RNA was studied by qPCR at day 7, 9, 14 and 21.

The present invention is based on the discovery that in infection studies with A549 cells, the results showed that in addition to EV1 infection, vemurafenib rescued the cells from coxsackie virus A9 and Coxsackie virus B3 infection in dose dependent manner with maximal inhibition at 5 μM (FIG. 1). Furthermore, all CVB serotypes from 1 to 6 were inhibited by vemurafenib (FIG. 2). Moreover, vemurafenib also efficiently rescued Min-6 pancreas cells from CVB4 infection (FIG. 3), A549 cells from polio-3 infection (FIG. 4) as well as Rhinovirus B14 infection (FIG. 5). In addition to the cell experiments, the efficacy of vemurafenib was proven in a mouse model where levels of infectious CVB4 were significantly decreased in pancreas and heart tissues (FIG. 6). Vemurafenib also attenuated viral induced effects in a transcriptomics study in acutely infected A549 cells (FIG. 7). It should be noted that in A549 cells, the mutation v600eBRAF, does not exist, so the effects during virus infection are supposedly not through BRAF at all (see also Oh et al. 2016). In accordance with this, also we found no effects in the transcriptomics study on BRAF. Importantly, vemurafenib totally eradicated CVB4 infection, both capsid and RNA, in persistently infected pancreas cells in vitro (FIG. 8).

Figure 9:
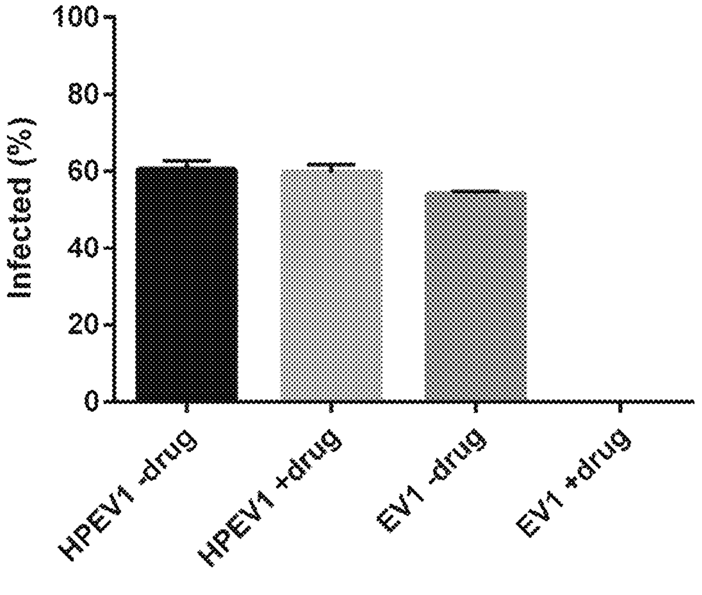
FIG. 9. Vemurafenib does not inhibit infection of human parechovirus 1 (HPEV1) belonging to the picornaviridae family. Vemurafenib (5 μM) was administered in A549 cells and it was present for the whole duration of the infection (6 h) of purified HPEV1. The cells show high infectivity, which was detected by the accumulation of capsid protein VP1 in the cell cytoplasm revealed by immunofluorescent labeling. Infection percentage was calculated by comparing VP1 positive cells to the total cell amount calculated based on DAPI staining. The results are mean±SD from two different experiments.
Figure 10:
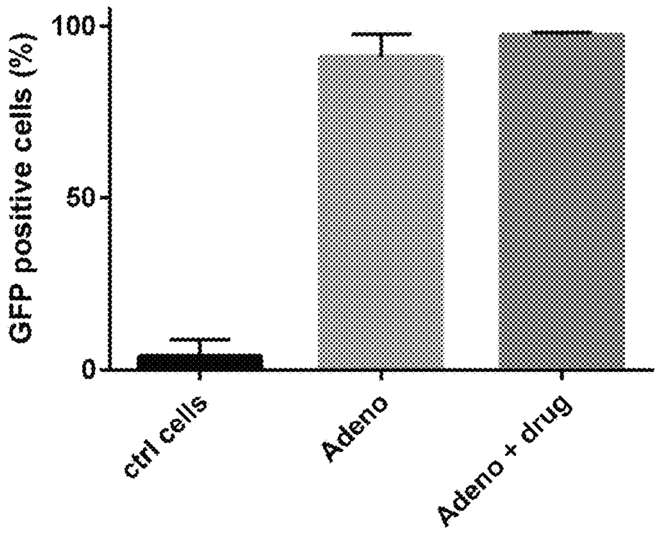
FIG. 10. Vemurafenib is not effective against adenoviruses. The effect on adenovirus 5 transduction was tested by using a GFP expression construct after an overnight exposure on A549 cells. The GFP fluorescence, proof of successful transduction, was similarly effective in the presence of 5 μM vemurafenib. The positive cells out of all cells were counted. The results show mean values from two experiments±SEM.
Figure 11:
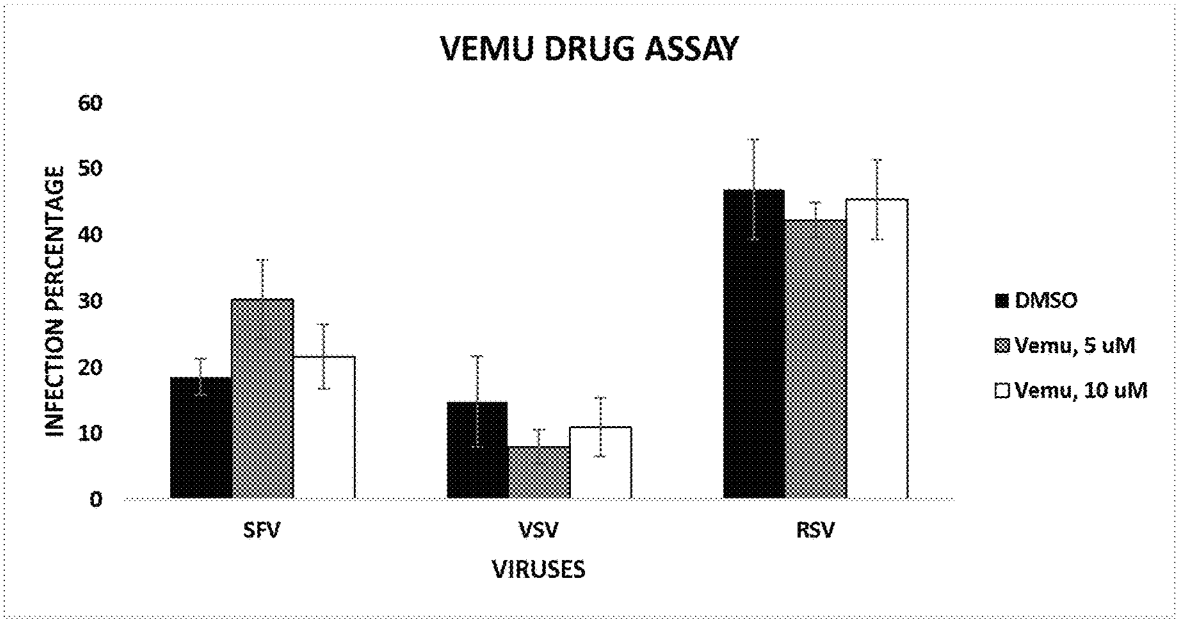
FIG. 11. Vemurafenib does not prevent the infection of semliki forest virus (SFV), vesicular stomatitis virus (VSV) and respiratory syncytial virus (RSV). Hela cells were pre-treated with 5 or 10 μM vemurafenib or DMSO as control for 30 min, after which GFP expressing variants of the viruses were added. The infection was allowed to proceed for 6 h (SFV and VSV) or 20 h (RSV) and the infection percentage was determined based on GFP fluorescence. The results are mean±SD from five replicates.

Vemurafenib was not effective against more distant members of picornaviruses, such as Human parechovirus 1 (FIG. 9). Furthermore, vemurafenib was not effective against adenovirus 5 (FIG. 10), nor Semliki Forest virus, Vesicular stomatitis virus or Respiratory syncytial virus (FIG. 11).

Figure 12:
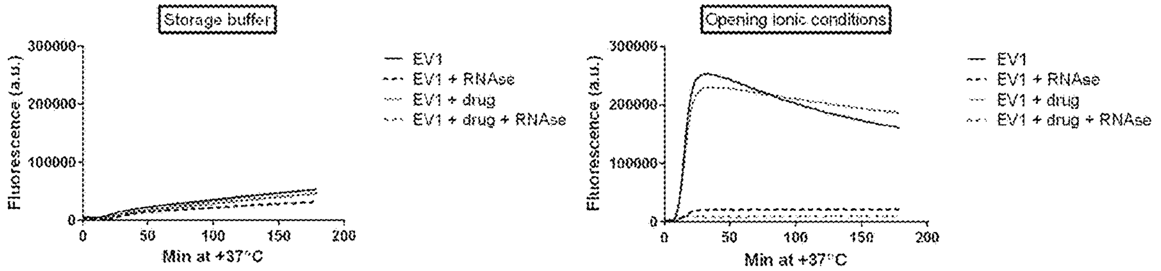
FIG. 12. Vemurafenib does not affect directly the EV1 virus particle, nor EV1 uncoating. Direct effects of vemurafenib on EV1 particle was studied using a real-time spectroscopic assay, where the viral opening was monitored using Sybr green II which intercalates with viral RNA causing an increase in fluorescence. The opening was studied in storage buffer conditions and ionic conditions which were recently discovered to cause opening of the virus (Ruokolainen et al., manuscript). Rnase was added to the reactions in order to separate the fluorescence that comes from the inside of the particle (porous particle) from the fluorescence of the released RNA outside the capsid.
Figure 13:
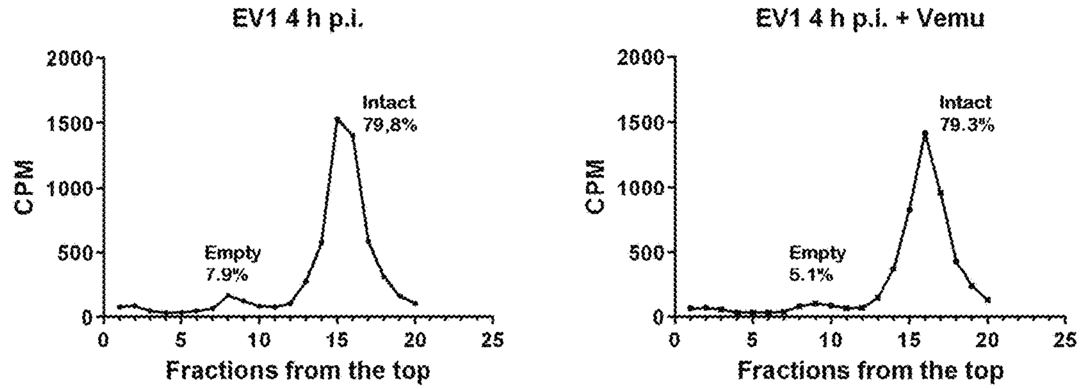
FIG. 13. Vemurafenib does not prevent uncoating of EV1 in cellular endosomes. Radioactively labeled EV1 particles were used to infect A549 cells. After 4 h p.i. the cell lysates were treated with detergent, collected and run in 5-20% sucrose gradients as described before. The proportional amount of empty and intact particles was calculated by dividing the CPM of incident fractions with the total CPM value. The gradients are representative results of 3 three different experiments.
Figure 14:
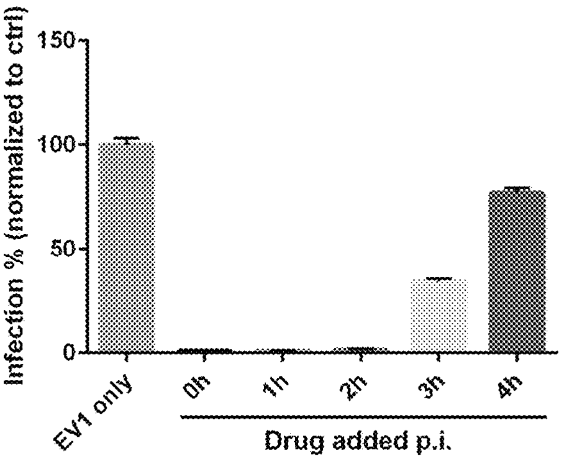
FIG. 14. Vemurafenib prevents the infection if added before 3 h p.i. A549 cells were infected with EV1 after which 5 μM vemurafenib was added at different times post infection (p.i.). The infection was followed until 6 h p.i. after which the cells were fixed with 4% PFA. The infection was determined by immunolabeling the viral capsid protein VP1 and comparing the amount of VP1 positive cells to the total cell amount calculated based on DAPI staining. The results were normalized to control infection where no drug was added (EV1 only). Values are means±SEM.
Figure 15:
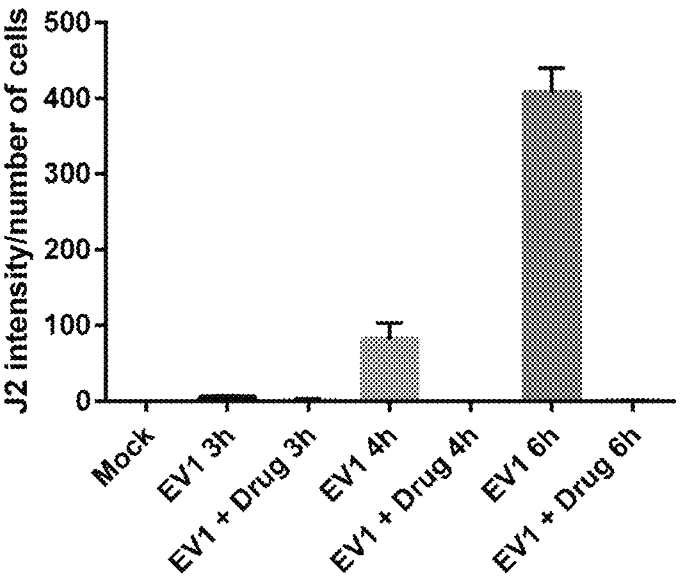
FIG. 15. Vemurafenib prevents replication detected by labeling of dsRNA. EV1 replication in A549 cells was measured in the presence or absence of 5 μM vemurafenib at 3, 4 or 6 h p.i. The dsRNA structures were immunolabeled with J2 antibody and the intensity of the signal was calculated using BioimageXD software. Also a control with no virus was included (mock) to determine the background of the antibody. The J2 intesity was normalized to the total number of cells determined by DAPI staining. Values are means±SEM.
Figure 16:
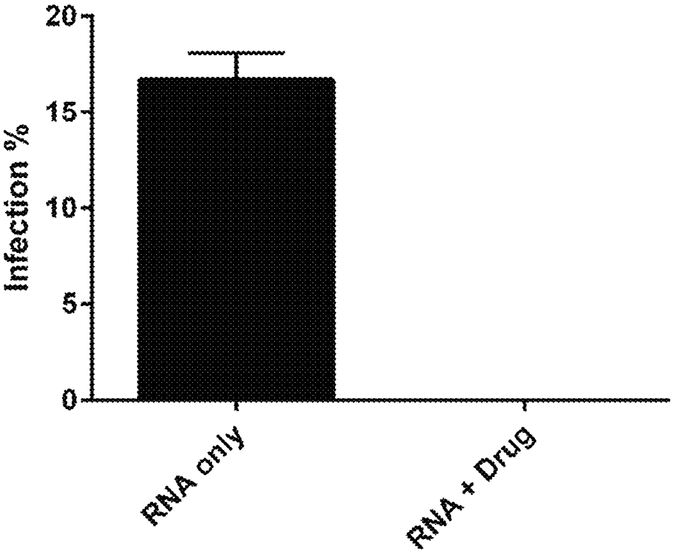
FIG. 16. Vemurafenib inhibits EV1 infection at the level of RNA transfected directly to the cytoplasm, i.e. bypassing the endosomal step, at the level of translation/replication. EV1 RNA was isolated using a high pure viral RNA isolation kit (Roche) according to the instructions of the manufacturer. A549 cells were transfected with viral RNA and the cells were incubated with or without 5 μM Vemurafenib at +37° C. for 6 h after which they were fixed with 4% PFA and labeled for VP1. The infection % was calculated by comparing the number of VP1 positive cells to the total cell number calculated based on DAPI staining. Values are means±SEM.
Figure 17:
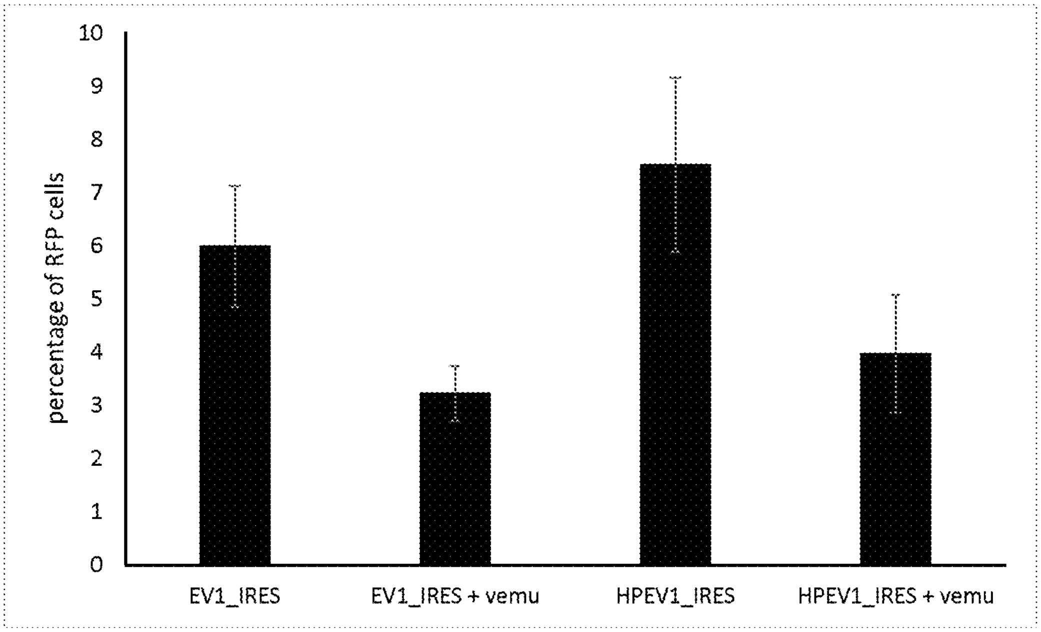
FIG. 17. Vemurafenib does not affect IRES-based translation. A plasmid containing either EV1 or HPEV1 IRES as a promoter for mCherry expression was used to study the effect of vemurafenib on IRES function. The plasmid was transfected into the cells with or without 5 μM vemurafenib and the function of IRES was determined based on mCherry fluorescence after 24 h, detected by microscopy. The results are mean from 4 replicates±SD.
Figure 18:
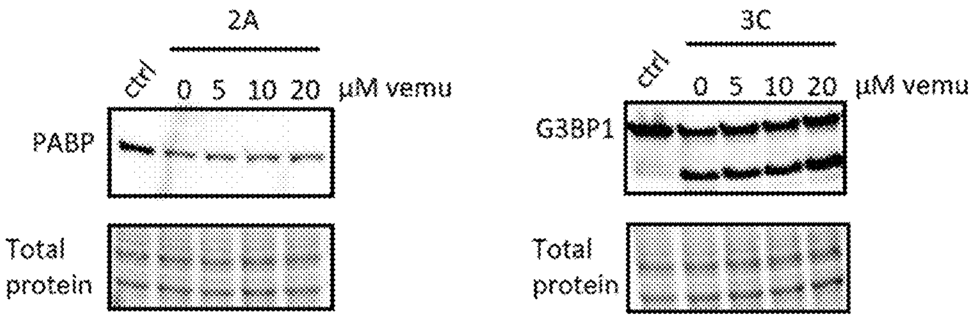
FIG. 18. Vemurafenib does not prevent the action of viral proteases 2A and 3C. The effect of vemurafenib on viral proteases was studied by treating Hela cell homogenate with purified 2A and 3C proteases with or without vemurafenib (5, 10 or 20 μM) being present. The results were detected by western blotting and known cellular targets for 2A and 3C, poly A binding protein (PABP) and stress granule assembly factor 1 (G3BP1) respectively, were immunolabeled. The results are representative of two separate experiments.
Figure 19:
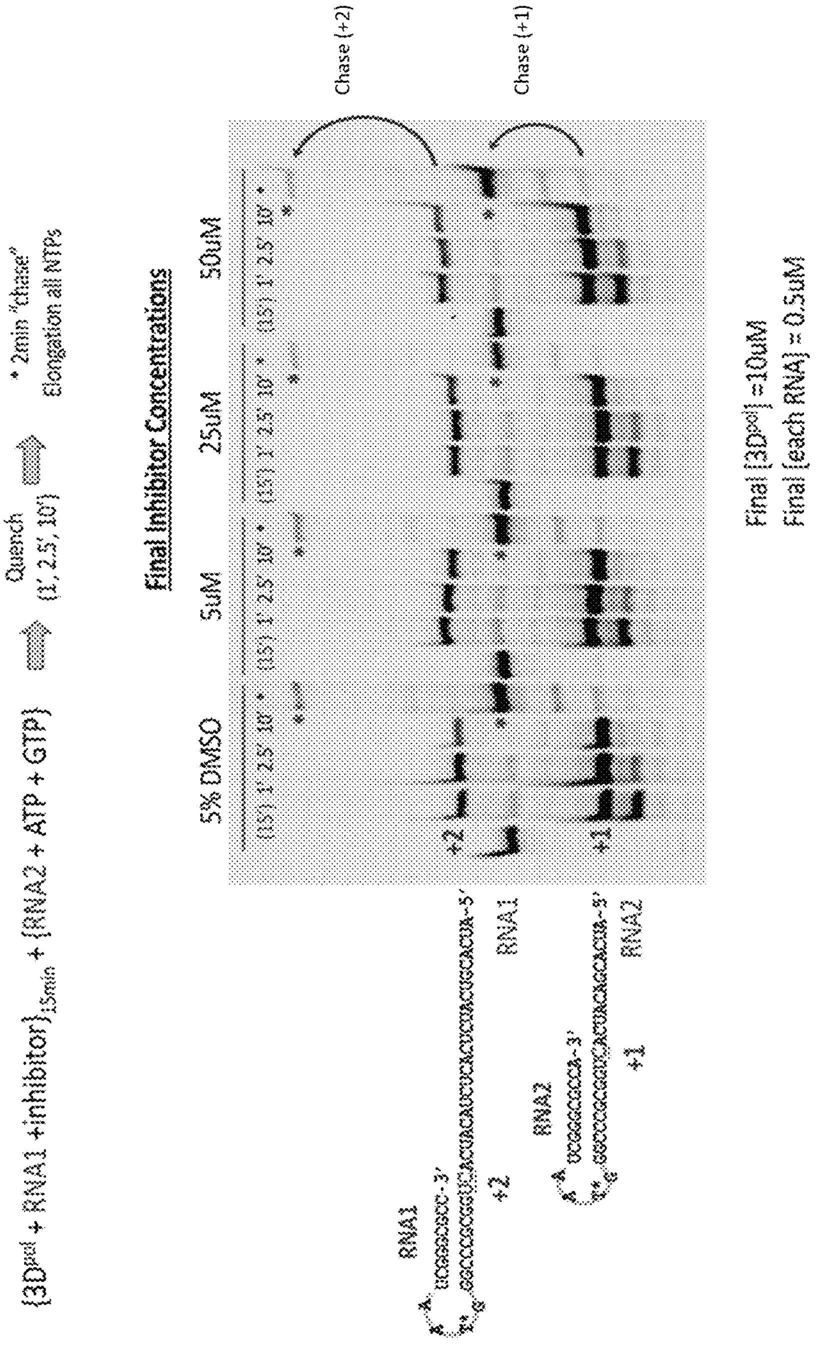
FIG. 19. Vemurafenib does not prevent the action of 3D polymerase. An RNA elongation assay was used to study the effect of vemurafenib on viral 3D polymerase. The 3D polymerase of CVB3 was incubated at RT for 15 min with RNA1 (SEQ ID NO:1) and various inhibitor concentrations or DMSO ctrl. At 15 min, GTP and ATP were added along with RNA2 (SEQ ID NO:2) allowing 3D+RNA1 complexes to incorporate ATP and GTP (forming +2 product) as well as initiate and incorporate GTP and RNA2 (forming +1 product). After 10 min, each reaction was "chased" to fully elongated product by adding the remaining NTPs.

Vemurafenib does not have direct virucidal effects on the virus based on spectroscopy fluorescent measurement, which shows that virus stays stable and does not release its genome upon drug treatment during 3 h at +37° C. (FIG. 12). In addition, vemurafenib does not affect the uncoating of EV1 inside endosomes in A549 cells (FIG. 13). Time of addition assays show that the efficacy of vemurafenib is lost if administered 3 h p.i. or later (FIG. 14). In addition, the replication of EV1 was prevented if vemurafenib was added on cells, indicated by measuring the amount of replication intermediate after various time periods (FIG. 15). Transfection of genomic RNA of EV1 in the presence of vemurafenib totally prevented infection proving that vemurafenib has effects on virus infection after the endosomal step (FIG. 16). Furthermore, Vemurafenib does not have direct effects on IRES-based translation (FIG. 17) nor on viral protease action by 2A or 3C (FIG. 18). In addition, in vitro experiment on CVB3 polymerase showed that vemurafenib does not prevent its action, nor binding or elongation of the nascent RNA chain (FIG. 19).

The present invention is thus based on the discovery that vemurafenib displays both potent and broad-spectrum activity against serotypes of several enterovirus species. Preferably against human enterovirus A, human enterovirus B, human enterovirus C, and human rhinovirus B.

Accordingly, the present invention is directed to a pharmaceutical product comprising vemurafenib or a pharmaceutically acceptable salt thereof for use in the treatment of an enteroviral infection.

Said enteroviral infection may cause poliomyelitis, polio-like syndrome, non-specific febrile illness, sepsis, aseptic meningitis, Bornholm disease, pericarditis, myocarditis, acute hemorrhagic conjunctivitis, herpangina, hand, foot and mouth disease, encephalitis, chronic fatigue syndrome, or type 1 diabetes.

A product or composition comprising vemurafenib or a salt thereof, may contain a pharmaceutically acceptable buffer, excipient, preservative, carrier or adjuvant, and may be administered orally or parenterally. The present invention thus provides pharmaceutical compositions comprising vemurafenib or a salt thereof, with pharmaceutically acceptable buffer, excipient, preservative, carrier or adjuvant for use in the treatment of enteroviral infections. In a multi-drug embodiment, said pharmaceutical composition further comprises a second anti-enteroviral agent, preferably said second anti-enteroviral agent is rupintrivir or enviroxime.

The phrase "pharmaceutically acceptable" refers herein to compositions that are physiologically tolerable and do not typically produce an allergic or similar reaction, when administered to a patient. Said pharmaceutical composition may also be formulated for sustained-release, delayed-release, or timed-release, or said pharmaceutical composition is a blend of sustained-release and immediate-release formulations.

The pharmaceutical product or composition may be administered orally in the form of a solid product such as a tablet, a granule, a powder, or a capsule. For the preparation of such a solid product, vemurafenib or a salt thereof may be combined with an appropriate additive, such as an excipient (e.g., lactose, mannitol, cornstarch, or crystalline cellulose), a binder (e.g., a cellulose derivative, acacia gum, or gelatin), a disintegrant (e.g., carboxymethylcellulose calcium), a preservative (e.g. L-ascorbic acid) or a lubricant (e.g., talc or magnesium stearate).

Such a solid product may be prepared into a controlled-release product by use of a coating base material such as hydroxymethylcellulose phthalate, hydroxypropylmethylcellulose acetate succinate, cellulose acetate phthalate, or methacrylate copolymer. The composition as defined in the claims may also be prepared into a liquid product such as a solution, a suspension, or an emulsion.

The composition comprising vemurafenib or a salt thereof, may be administered parenterally in the form of an injection. For the preparation of an injection, the composition may be combined with, for example, water, ethanol, glycerin, or a conventionally employed surfactant. The composition may also be prepared into a suppository by use of an appropriate base material.

The composition comprising vemurafenib or a salt thereof, may be administered in combination with a second anti-enteroviral agent employed in multi-drug combination therapy, in which said composition and the second anti-enteroviral agent may be administered simultaneously or separately at the same frequency of dosage or different frequencies through the same administration method or different administration methods.

The second anti-enteroviral agent may include but is not limited to compounds such as ribavirin, Pirodavir, Pleconaril, V-073, Rupintrivir (AG-7088), 2'-C-Met-Cyt, Enviroxime, TTP-8307 and MDL-860. It will also be understood that the second anti-enteroviral agent may be interferon or a vaccine such as a polio vaccine (OPV-Sabin or IPV-Salk).

The actual dosage amount of the vemurafenib or a salt thereof (e.g., an effective amount) that is administered to a patient can be determined by physical and physiological factors such as body weight, severity of condition, the type of disease being treated, previous or concurrent therapeutic interventions, and on the route of administration. The practitioner responsible for administration can determine the concentration of active ingredient(s) in a composition and appropriate dose(s) for the individual subject.

The pharmaceutical products or compositions disclosed herein are preferably prepared for storage by mixing the compound having the desired degree of purity with optional physiologically acceptable carriers (such as nanocarriers), excipients, preservatives or stabilizers (Remington's Pharmaceutical Sciences, 22nd edition, Allen, Loyd V., Jr, Ed., (2012)), in the form of a solid or aqueous solutions. Acceptable carriers, excipients, preservatives or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

Vemurafenib or a salt thereof may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

In an embodiment, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

In other non-limiting examples, a dose of a pharmaceutical composition or formulation can comprise from about 1 milligram/kg/body weight, about 5 milligram/kg/body weight, about 10 milligram/kg/body weight, about 20 milligram/kg/body weight, about 25 milligram/kg/body weight, about 30 milligram/kg/body weight, about 35 milligram/kg/body weight, about 40 milligram/kg/body weight, to about 100 mg/kg/body weight of vemurafenib or a salt thereof per administration, and any range derivable therein. The preferred dose of vemurafenib is 960 mg (4 tablets of 240 mg) twice daily (equivalent to a total daily dose of 1,920 mg). Preferably, the first dose is to be taken in the morning and the second dose is to be taken approximately 12 hours later in the evening.

In a preferred embodiment, the present pharmaceutical product comprises vemurafenib in its amorphous or polymorphic form.

In another preferred embodiment, said product comprises hydroxypropyl methylcellulose acetate succinate (HPMC-AS).

In another preferred embodiment, said product comprises a salt of vemurafenib such as vemurafenib hydrochlorid.

According to the current taxonomy, the following ten species are now included in the genus Enterovirus: human enterovirus A, human enterovirus B, human enterovirus C, human enterovirus D, bovine enterovirus, porcine enterovirus B, simian enterovirus A, human rhinovirus A, human rhinovirus B and human rhinovirus C. The four species of human enterovirus include the polioviruses, group A and B coxsackieviruses, echoviruses and enterovirus serotypes. Within the species human enterovirus A-D, the enterovirus serotypes may be categorised as non-polio enterovirus serotypes (an expression used herein to embrace group A and B coxsackieviruses, echoviruses and enterovirus serotypes from EV68 onwards) and poliovirus serotypes.

In a preferred embodiment, said enteroviral infection is caused by a serotype of one or more of the species of human enterovirus A, human enterovirus B, human enterovirus C, and human rhinovirus B, preferably by a serotype of one or more of the species of human enterovirus B, human enterovirus C, and human rhinovirus B.

In another preferred embodiment, the serotype of human enterovirus C is a poliovirus.

In another preferred embodiment, the enterovirus serotype is a non-polio enterovirus. In another preferred embodiment, the enterovirus serotype is selected from the group consisting of coxsackieviruses A, coxsackieviruses B, rhinoviruses B, polioviruses and echoviruses.

The present invention is also directed to the corresponding methods of treatment as disclosed in the appended claims.

In a further embodiment, the present invention is directed to an in vitro method of screening enteroviruses for identifying those enteroviral serotypes the infection of which is inhibited, attenuated or prevented by vemurafenib, the method comprising the steps of culturing or providing host cells, preferably human host cells, in a culture medium, contacting said host cells with an enteroviral serotype and vemurafenib in any order and incubating the infected host cells in order to identify those enteroviral serotypes the infection of which is inhibited, attenuated or prevented by vemurafenib. Preferably, the enteroviral serotype to be tested in the method is selected from the group consisting of the enterovirus species A-L and rhinovirus species A-C.

Bibliographic details of references provided in the subject specification are listed at the end of the specification. Reference to any art is not, and should not be taken as an acknowledgment or any form of suggestion that this art forms part of the common general knowledge in any country. The present invention is further described in the following examples, which are not intended to limit the scope of the invention.

EXAMPLES

Example 1

Vemurafenib prevents the infection of EV1, CVA9 and CVB3 in dose dependent manner. Adenocarcinoma human alveolar basal epithelial (A549, ATCC) cells were cultured in Dulbecco's modified eagle medium (DMEM; Gibco) supplemented with 10% fetal bovine serum (FBS; Gibco), 1% Glutamax (Gibco) and 1% penicillin and streptomycin antibiotics (Gibco) for 24 h. Next day, the cells were treated for 1 h with different concentrations of vemurafenib diluted in DMEM supplemented with 1% FBS and 1% glutamax and then infected with EV1 (ATCC; Farouk strain), CVB3 (ATCC; Nancy strain) or CVA9 (ATCC; Griggs strain) and vemurafenib was present after addition of viruses. In addition, non-infected control cells were included. After 18 h post infection (p.i.), the cell viability was determined by cell titer-Glo assay according to the instructions by the manufacturer (CTG assay, which measures cellular ATP levels, Promega; left figure) or crystal violet staining as described before (right figure; Martikainen et al. 2015). The results are shown in FIG. 1. Values are means±SD.

Example 2

Vemurafenib prevents the infection of different CVB serotypes in dose dependent manner. A549 cells were cultured in DMEM supplemented with 10% FBS, 1% Glutamax and 1% penicillin and streptomycin antibiotics for 24 h, after which the cells were treated for 1 h with different concentrations of vemurafenib diluted in DMEM supplemented with 1% FBS and 1% glutamax. Next, the cells were infected with different CVB serotypes 1-6 (ATCC) and the infection was allowed to proceed at +37° C. for 18 h in the presence of the drug. Finally, the cell viability was determined using crystal violet staining. The results were normalized to control sample with no virus infection and 0 μM concentration of vemurafenib (CTRL). The results are shown in FIG. 2. The values are means±SD.

Example 3

Figure 3:
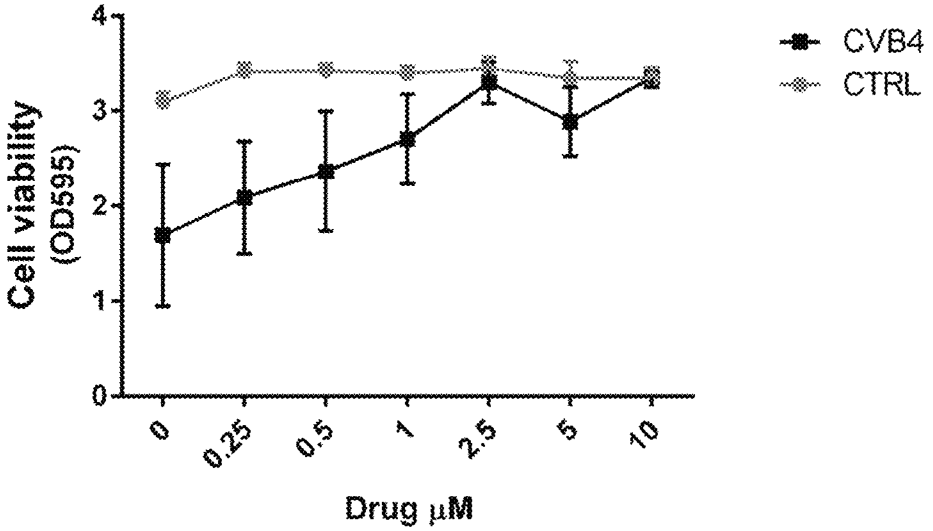
FIG. 3. Vemurafenib prevents the infection of CVB4 in pancreatic beta cell line in dose dependent manner. Mouse pancreatic beta cell line, Min-6 cells, were treated with different concentrations of vemurafenib and infected or not with CVB4. The viability of cells was determined using crystal violet staining. The values are means±SD.

Vemurafenib prevents the infection of CVB4 in pancreatic beta cell line in dose dependent manner. The effect of Vemurafenib on the CVB4 E2 diabetogenic strain (provided by Ji-Won Yoon, Julia McFarlane Diabetes Research Center, Calgary, Alberta, Canada) induced CPE was studied in a mouse pancreatic beta cell line Min-6-cells (Kindly provided by A. Abderrahmani, Lille France). First, the cells were seeded in 96-well tissue culture plates ($10^4$ cells/well/100 μl) in DMEM (Gibco, Invitrogen) supplemented with 15% fetal calf serum (FCS, Sigma), 1% L-glutamine (Gibco), 50 μg/ml streptomycin, and 50 IU/ml penicillin (BioWhittaker) and incubated for 24 h at 37° C., 5% CO2. The next day, Vemurafenib was added at a final concentration of 0.25, 0.5, 1, 2.5, 5 and 7.5 μM and incubated for 1 h at 37° C. after which 10 μl of CVB4E2 was added to obtain an MOI of 1. The plates were incubated at 37° C. with a humidified atmosphere at 5% CO2. The viability of the cells was assessed using crystal violet stain. The results are shown in FIG. 3. The values are means±SD.

Example 4

Vemurafenib prevents the infection of Poliovirus 3 in dose dependent manner. Different concentrations of vemurafenib were tested against polio-3 (vaccine strain) by treating A549 cells with the drug for 1 h and then infecting the cells with the virus. Cell viability was determined using Cell Titer Glo kit (Promega) after 2 days of infection. The results are shown in FIG. 4. The results are means±SD.

Example 5

Vemurafenib decreases the replication of human rhinovirus B14 (HRVB14) indicated by labeling of dsRNA. Hela MZ cells (Kind gift from Marino Zerial, Max-Planck Institute, Dresden) were grown on coverslips in DMEM supplemented with 10% FBS, 1% Glutamax and 1% penicillin/streptomycin antibiotics for 24 h. The next day, cells were infected with HRVB14 (ATCC) with or without 5 μM vemurafenib and infection was allowed to proceed for 6 h at +34° C. in DMEM supplemented with 1% FBS and 1% Glutamax. After fixation with 4% PFA, the cells we immunolabeled with dsRNA antibody (J2, Scicons) and corresponding Alexa fluor-488 conjugated secondary antibody (Molecular probes, Invitrogen/USA) in order to determine the status of replication. The intensity of J2 signal was calculated using BioimageXD software. The J2 intesity was normalized to the total number of cells determined by DAPI staining. Finally the results were normalized to HRVB14 infection without the drug which was set to 100%. The results are shown in FIG. 5. Values are means from two separate experiments±SD.

Example 6

Vemurafenib decreases the levels of infectious CVB4 viral particles in the heart and pancreas tissue of mice. Hsd:ICR(CD-1) female mice were provided by ENVIGO (Gannat, France) and handled in specific "pathogen-free" conditions and according to the guidelines of 2010 EU directory. Experiments on mice were approved by the local Ethical Committee for Animal Experimentation (C2EA-75 Nord-Pas-de-Calais, France).

Hsd:ICR(CD-1) female mice at the age of 3 weeks were inoculated intraperitoneally with Vemurafenib dissolved in DMSO and diluted in PBS (10 mg/kg) or with DMSO diluted in PBS once a day (starting on day 1) for 5 days. The animals were inoculated intraperitoneally with CV-B4 E2 ($6\times10^6$ TCID50 in 200 μL PBS) on day 2. The animals were sacrificed on day 6, blood was collected and portions of each organ (pancreas and heart) were frozen for determination of viral titer. Frozen organs were weighed, crushed using a tissue ruptor (Qiagen®, France), homogenized in 0.5 ml of PBS and then centrifuged at 2000 g for 10 min 4° C. The supernatants were harvested to measure the titer of infectious particles on HEp-2 cells (BioWhittaker). Hep-2 cells were cultured in Eagle's minimum essential medium (MEM; Gibco) supplemented with 10% FCS, 1% 1-glutamine and 1% antibiotic (50 μg/ml streptomycin, and 50 IU/ml penicillin (BioWhittaker). Virus titers were determined by limiting dilutions assay for 50% tissue culture infectious doses ($TCID_{50}$) by the method of Reed-Muenchand and the titers were normalized to tissue weight. The results were expressed as log TCID50/g. The limit of detection of the test was 0.75 log TCID50/g. The results are shown in FIG. 6.

Example 7

Vemurafenib shows efficacy in mRNA level during EV1 infection. A transcriptomics study was performed in A549 cells+/−treatment with vemurafenib in the presence or absence of EV1 infection. RNA was extracted from EV1- or mock-infected A549 cells 6 h pi. using RNeasy Mini kit (Qiagen). Gene expression profiling was done using Illumina Human HT-12 v4 Expression BeadChip Kit according to manufacturer's recommendation. Genes differentially expressed between samples and controls were determined using the Limma package. Benjamini-Hocberg multiple correction testing method was used to filter out differentially expressed genes based on a q-value threshold ($q<0.05$). Filtered data were sorted by logarithmic fold change (log 2Fc). The data revealed the efficacy of the drug on mRNA level. Several different mRNAs were up- or downregulated due to EV1 but the drug attenuated almost all the effects of the virus. The results are shown in FIG. 7.

Example 8

Vemurafenib eradicates persistent CVB4 infection. Persistently-infected Panc-1 cells (described in Alidjinou et al. 2015) were cultured in 6-well plate, and treated with 7.5 μM of vemurafenib each 2 to 3 days. The cells were subcultured once a week. Supernatants were collected before each treatment renewal, and conserved at −80° C. before titration.

Supernatants were 10-fold diluted and added to HEp-2 cells (BioWhittaker) to determine the level of infectious viral particles of treated and untreated cells. Virus titers were determined by limiting dilutions assay for 50% tissue culture infectious doses ($TCID_{50}$) by the method of Reed-Muenchand. In addition, the presence of viral RNA was studied by qPCR at day 7, 9, 14 and 21. Total RNA was extracted, and RT-PCR targeting viral RNA was performed. The results are shown in FIG. 8.

Example 9

Vemurafenib is not effective against adenoviruses. The effect on adenovirus 5 transduction was tested by using a GFP expression construct (EATRIS National Virus Vector Laboratory, Kuopio, Finland). A549 cells were cultured on 6-well plates in DMEM supplemented with 10% FBS, 1% Glutamax and 1% penicillin/streptomycin antibiotics for 24 h. The next day, the cells were infected with Adeno5-GFP in DMEM supplemented with 1% FBS and 1% Glutamax with or without 5 μM vemurafenib. The infection was allowed to proceed at +37° C. for 17 h after which the cells were trypsinized and then fixed with 4% PFA. The GFP fluorescence, proof of successful transduction, was studied by flow cytometry (Guava easycyte, Merck Millipore). The positive cells out of all cells were counted. The results are shown in FIG. 10. The results show mean values from two experiments±SEM.

Example 10

Vemurafenib does not inhibit infection of human parechovirus 1 (HPEV1) belonging to the picornaviridae family. A549 cells were grown on coverslips in DMEM supplemented with 10% FBS, 1% Glutamax and 1% penicillin/streptomycin antibiotics for 24 h. The next day, cells were infected with HPEV1 (Griggs strain, ATCC) with or without 5 μM vemurafenib and infection was allowed to proceed for 6 h at +37° C. in DMEM supplemented with 1% FBS and 1% Glutamax. After fixation with 4% PFA, capsid protein VP1 was immunolabeled with a primary antibody (Marjomäki et. al 2002) followed by labeling with corresponding Alexa fluor-555 conjugated secondary antibody (Molecular probes, Invitrogen/USA). Infection percentage was calculated by comparing VP1 positive cells to the total cell amount calculated based on DAPI staining. The results shown in FIG. 9 are mean±SD from two different experiments.

Example 11

Vemurafenib does not prevent the infection of semliki forest virus (SFV), vesicular stomatitis virus (VSV) and respiratory syncytial virus (RSV). Hela cells were pretreated with 5 or 10 μM vemurafenib or DMSO as control for 30 min, after which GFP expressing variants of the viruses were added: SFV-ZsG, strain SFV4 (Spuul et al., 2010); VSV-GFP, Indiana strain (Pelkmans et al., 2005); RSV-GFP, A2 strain (Krzyzaniak et al., 2013). The infection was allowed to proceed for 6 h (SFV and VSV) or 20 h (RSV) and the infection percentage was determined by microscopy based on GFP fluorescence. The results shown in FIG. 11 are mean±SD from five replicates.

Example 12

Vemurafenib does not affect directly the EV1 virus particle, nor EV1 uncoating. Direct effects of vemurafenib (5 μM) on EV1 particle was studied using a real-time spectroscopic assay, where the viral opening was monitored using Sybr green II (Invitrogen) which intercalates with viral RNA causing an increase in fluorescence (Myllynen et al. 2016). The opening was studied in storage buffer conditions (2 mM $MgCl_2$ in PBS) and ionic conditions which were recently discovered to cause opening of the virus (Ruokolainen et al., manuscript). Rnase was added to the reactions in order to separate the fluorescence that comes from the inside of the particle (porous particle) from the fluorescence of the RNA Example 13

Vemurafenib does not prevent uncoating of EV1 in cellular endosomes. Radioactively labeled EV1 particles (described in Myllynen et al. 2016) were used to infect A549 cells with or without 5 μM vemurafenib being present. After 4 h p.i. the cell lysates were treated with 100 mM Octylglucopyranoside (Amresco) diluted in 2 mM $MgCl_2$ in PBS for 30 min on ice. Finally, the cell lysates were run in 5-20% sucrose gradients as described before (Myllynen et al. 2016). The proportional amount of empty and intact particles was calculated by dividing the CPM of incident fractions with the total CPM value. The gradients are representative results of 3 three different experiments. The results are shown in FIG. 13.

Example 14

Vemurafenib prevents the infection if added before 3 h p.i. A549 cells were grown on coverslips in DMEM supplemented with 10% FBS, 1% Glutamax and 1% penicillin/streptomycin antibiotics for 24 h. The next day, EV1 was bound on ice for 1 h in 1% DMEM supplemented with 1% FBS and 1% Glutamax. After excess virus was washed, the infection was allowed to proceed at +37° C. and 5 μM vemurafenib was added at different times post infection (p.i.). The infection was followed until 6 h p.i. after which the cells were fixed with 4% PFA. The viral capsid protein VP1 was immunolabeled with anti-EV1 antibody (Marjomäki et. al 2002) and corresponding Alexa fluor-555 conjugated secondary antibody (Molecular probes, Invitrogen/USA). The infection was determined by comparing the amount of VP1 positive cells to the total cell amount calculated based on DAPI staining. The results shown in FIG. 14 were normalized to control infection where no drug was added (EV1 only). Values are means±SEM.

Example 15

Vemurafenib prevents replication detected by labeling of dsRNA. A549 cells were grown on coverslips in DMEM supplemented with 10% FBS, 1% Glutamax and 1% penicillin/streptomycin antibiotics for 24 h. The infection was carried out by binding EV1 first on ice for 1 h in 1% DMEM supplemented with 1% FBS and 1% Glutamax and washing the excess virus away. Next, and the infection was allowed to proceed at +37° C. for 3, 4 or 6 h with or without 5 μM vemurafenib in 1% DMEM supplemented with 1% FBS and 1% Glutamax, after which the cells were fixed with 4% PFA. The dsRNA structures were immunolabeled with J2 antibody (Scicons), and corresponding Alexa fluor-488 conjugated secondary antibody (Molecular probes, Invitrogen/USA). The intensity of the signal was calculated using BioimageXD software. Also a control, cells with no virus was included (mock) to determine the background of the antibody. The J2 intesity was normalized to the total number of cells determined by DAPI staining. The results are shown in FIG. 15. Values are means±SEM.

Example 16

Vemurafenib inhibits EV1 infection at the level of RNA transfected directly to the cytoplasm, i.e. bypassing the endosomal step, at the level of translation/replication. EV1 RNA was isolated using a high pure viral RNA isolation kit (Roche) according to the instructions of the manufacturer. A549 cells were cultivated on coverslips in 4-well plates until sub-confluency in DMEM supplemented with 10% FBS, 1% Glutamax and 1% penicillin/streptomycin antibiotics. According to the manufacturer's instructions, 750 ng of viral RNA was transfected into the cells per well using Lipofectamine 3000. The cells were incubated with or without 5 μM Vemurafenib in DMEM supplemented with 5% FBS and 1% glutamax at +37° C. for 6 h, after which they were fixed with 4% PFA and labeled for VP1 (Marjomäki et. al 2002) and corresponding Alexa fluor-555 conjugated secondary antibody (Molecular probes, Invitrogen/USA). The infection % was calculated by comparing the number of VP1 positive cells to the total cell number calculated based on DAPI staining. The results are shown in FIG. 16. Values are means±SEM.

Example 17

Vemurafenib does not affect IRES-based translation. A DNA plasmid (pTM1) contained T7 promoter followed by the IRES of either EV1 Farouk strain (AAAA-0084-pTM1-F-EV1-mCherry-NLS) or HPEV1 strain 22 Harris (AAAA-0083-pTM1-HPEV1_22-mCherry-NLS), and mCherry after respective IRES sequence. mCherry expression was used as a readout to study the effect of vemurafenib on IRES function in fluorescence microscopy. According to the instructions of the manufacturer 0.3 μg of DNA was transfected into doxicyclin-inducible T7 polymerase expressing Hela cells (kind gift from Giuseppe Balistreri, University of Helsinki, Finland) using Lipofectamine 3000. The cells were incubated with or without 5 μM Vemurafenib in DMEM supplemented with 10% FBS and 1% glutamax at +37° C. for 24 h, after which the cells were fixed with 4% PFA. The function of IRES was determined based on mCherry fluorescence detected by microscpy. The results shown in FIG. 17 are mean from 4 replicates±SD.

Example 18

Vemurafenib does not prevent the action of viral proteases 2A and 3C. The effect of vemurafenib on viral proteases was studied by treating 72 μg of Hela cell homogenate (prepared as described before in Feng et al. 2014) with 0.4 μg of purified 2A and 3C proteases (Laitinen et al. 2018). The reaction was carried out in buffer containing 20 mM HEPES (pH 7.4), 0.12 M $KCH_3COO$, 4 mM $Mg(CH_3COO)_2$ and 5 mM DTT with or without vemurafenib (5, 10 or 20 μM) being present. The reactions were carried out at RT for 18 h, after which they were terminated by adding Laemmli sample buffer and heating at 100° C. for 9 min. The samples were run in 4-20% Miniprotean TGX stain free gel (Biorad). The gel was UV-activated for 5 min with Chemidoc MP (Biorad) to reveal the total protein amount, after which the proteins were transferred to PVDF membrane (Immobilon-P, Merck Millipore). Next, the blot was blocked o/n with 5% BSA in 0.05% tween in TBS. Poly A binding protein (PABP) was detected using 1:100 dilution of mouse anti-PABP (Santa Cruz). Stress granule assembly factor 1 G3BP1 was detected using 1:1000 dilution of mouse anti-G3BP1 (Santa Cruz). The results are shown in FIG. 18.

Example 19

Vemurafenib does not prevent the action of 3D polymerase. An RNA elongation assay was used to study the effect of vemurafenib on viral 3D polymerase. The 3D polymerase of CVB3 was incubated at RT for 15 min with RNA1 (SEQ ID NO:1) and various inhibitor concentrations or DMSO ctrl. At 15 min, GTP and ATP were added along with RNA2 (SEQ ID NO: 2) allowing 3D+RNA1 complexes to incorporate ATP and GTP (forming +2 product) as well as initiate and incorporate GTP and RNA2 (forming +1 product). After 10 min, each reaction was "chased" to fully elongated product by adding the remaining NTPs. The results are shown in FIG. 19.

REFERENCES

Cited Non-Patent Literature

Alidjinou E K, Sane F, Bertin A, Caloone D, Hober D. Persistent infection of human pancreatic cells with Coxsackievirus B4 is cured by fluoxetine. Antiviral Res. 2015 April; 116:51-4. doi: 10.1016/j.antiviral.2015.01.010. Epub 2015 Feb. 2.

Bollag G, Hirth P, Tsai J, et al. Clinical efficacy of a RAF inhibitor needs broad target blockade in BRAF-mutant melanoma. Nature. 2010; 467(7315):596-599. doi: 10.1038/nature09454.

Chapman P B, Hauschild A, Robert C, et al. Improved Survival with Vemurafenib in Melanoma with BRAF V600E Mutation. The New England journal of medicine. 2011; 364(26):2507-2516. doi: 10.1056/NEJMoa1103782.

Krzyzaniak, M. A., Zumstein, M. T., Gerez, J. A., Picotti, P., & Helenius, A. (2013). Host Cell Entry of Respiratory Syncytial Virus Involves Macropinocytosis Followed by Proteolytic Activation of the F Protein. *PLoS Pathogens,* 9 (4), e 1003309.

Laitinen, O. H,. E. Svedin, S. Kapell, M. M. Hankaniemi, P. G. Larsson, E. Domsgen, V. M. Stone, J. A. E. Maatta, H. Hyoty, V. P. Hytonen, et al. (2018). New Coxsackievirus 2A (pro) and 3C(pro) protease antibodies for virus detection and discovery of pathogenic mechanisms, J Virol Methods, 255, pp. 29-37.

Marjomäki, V., Pietiäinen, V., Matilainen, H., Upla, P., Ivaska, J., Nissinen, L., Heino, J., (2002). Internalization of Echovirus 1 in Caveolae. Journal of Virology, 76 (4), 1856-1865.

Martikainen, M., Salorinne, K., Lahtinen, T., Malola, S., Häkkinen, H., Marjomäki, V., 2015, Hydrophobic pocket targeting probes for enteroviruses. Nanoscale, 7(41): 17457-67.

McKimm-Breschin, J., Fry, A M., 2016, Meeting report: $4^{th}$ ISIRV antiviral group conference: Novel antiviral therapies for influenza and other respiratory viruses. Antiviral Research, 129:21-38.

Myllynen, M., Kazmertsuk, A., Marjomäki, V., 2016, A Novel Open and Infectious Form of Echovirus 1. J Virol. 90 (15): 6759-70.

Oh, Y., Deng, J., Yue, P., & Sun, S. (2016). Paradoxical activation of MEK/ERK signaling induced by B-Raf inhibition enhances DR5 expression and DR5 activation-induced apoptosis in Ras-mutant cancer cells. Scientific reports.

Pelkmans L, Fava E, Grabner H, Hannus M, Habermann B, Krausz E, Zerial M. (2005) Genome-wide analysis of human kinases in clathrin- and caveolae/raft-mediated endocytosis. Nature; 436:78-86.

Qian Feng, Martijn, A. Langereis, Marie Lork, Mai Nguyen, Stanleyson, V. Hato, Kjerstin La nke, LuniEmdad, Praveen Bhoopathi, Paul B. Fisher, Richard E. Lloyd, Frank J. M. van Kuppeveld (2014). Enterovirus $2A^{pro}$ Targets MDA5 and MAVS in Infected Cells. Journal of Virology.

Spuul, P., Balistreri, G., Hellström, K., Golubtsov, A. V., Jokitalo, E., Ahola, T., (2011), Assembly of Alphavirus Replication Complexes from RNA and Protein Components in a Novel trans-Replication System in Mammalian Cells. Journal of Virology, 85 (10) 4739 4751

Cited Patent Literature

US20160068530
US20170320872
WO 9418960
WO 2011160191
WO 2007002433
WO 2016165678
WO 2018002415
WO 2014056894
WO 2017147526

The invention claimed is:

1. A method for treating, alleviating, or reducing an enteroviral infection caused by an enterovirus comprising administering a pharmaceutical product comprising vemurafenib or a pharmaceutically acceptable salt thereof to a subject suffering from said enteroviral infection, wherein the enterovirus is selected from the group consisting of coxsackieviruses B and polioviruses.

2. The method according to claim 1, wherein said product comprises vemurafenib in its amorphous form.

3. The method according to claim 1, wherein said product comprises hydroxypropyl methylcellulose acetate succinate (HPMC-AS).

4. The method according to claim 1, wherein said product comprises vemurafenib hydrochloride.

5. The method according to claim 1, wherein said enteroviral infection causes poliomyelitis, polio-like syndrome, pericarditis, myocarditis, or type 1 diabetes.

6. The method according to claim 1, wherein said product comprises at least one pharmaceutically acceptable buffer, carrier, excipient, preservative or adjuvant.

7. The method according to claim 1, wherein the product is a tablet and the tablet comprises colloidal anhydrous silica, croscarmellose sodium, hydroxypropylcellulose, and magnesium stearate as excipients.

8. The method according to claim 1, wherein said product is formulated for sustained-release, delayed-release, or timed-release, or said product comprises a blend of sustained-release and immediate-release formulations.

9. The method according to claim 1, wherein said enteroviral infection is caused by a coxsackie B virus.

10. The method according to claim 9, wherein said enteroviral infection causes pericarditis, myocarditis or type 1 diabetes.

11. The method according to claim 10, wherein said enteroviral infection is caused by coxsackie B virus 4 (CVB4).

12. The method according to claim 1, wherein said enteroviral infection is caused by a poliovirus.

13. The method according to claim 12, wherein said enteroviral infection causes poliomyelitis or a polio-like syndrome.

14. The method according to claim 13, wherein said enteroviral infection is caused by poliovirus 3.

* * * * *